(12) United States Patent
Trattler et al.

(10) Patent No.: US 10,925,497 B2
(45) Date of Patent: Feb. 23, 2021

(54) CIRCUIT ARRANGEMENT FOR AN OPTICAL MONITORING SYSTEM AND METHOD FOR OPTICAL MONITORING

(71) Applicant: ams AG, Unterpremstaetten (AT)

(72) Inventors: Peter Trattler, Seiersberg-Pirka (AT); Manfred Pauritsch, Graz (AT); Herbert Lenhard, Graz (AT)

(73) Assignee: ams AG, Unterpremstätten (AT)

( * ) Notice: Subject to any disclaimer, the term of this patent is extended or adjusted under 35 U.S.C. 154(b) by 560 days.

(21) Appl. No.: 15/752,238

(22) PCT Filed: Aug. 17, 2016

(86) PCT No.: PCT/EP2016/069520
§ 371 (c)(1),
(2) Date: Feb. 12, 2018

(87) PCT Pub. No.: WO2017/032664
PCT Pub. Date: Mar. 2, 2017

(65) Prior Publication Data
US 2020/0037901 A1    Feb. 6, 2020

(30) Foreign Application Priority Data
Aug. 26, 2015  (EP) .................................... 15182575

(51) Int. Cl.
*A61B 5/024* (2006.01)
*A61B 5/0245* (2006.01)
(Continued)

(52) U.S. Cl.
CPC ........ *A61B 5/02416* (2013.01); *A61B 5/7221* (2013.01); *A61B 2560/0209* (2013.01); *H04B 10/07* (2013.01)

(58) Field of Classification Search
CPC .............. A61B 5/02416; A61B 5/7221; A61B 2560/0209; A61B 5/14552; A61B 5/024;
(Continued)

(56) References Cited

U.S. PATENT DOCUMENTS

| 4,453,218 A | 6/1984 | Sperinde et al. |
|---|---|---|
| 5,153,875 A | 10/1992 | Takatori |

(Continued)

FOREIGN PATENT DOCUMENTS

| CN | 1747367 A | 3/2006 |
|---|---|---|
| CN | 100492840 C | 5/2009 |

(Continued)

OTHER PUBLICATIONS

AFE4400 "Integrated Analog Front-End for Heart Rate Monitors and Low-Cost Pulse Oximeters" Texas Instruments Incorporated; 2012-2014.

(Continued)

*Primary Examiner* — Huan H Tran
(74) *Attorney, Agent, or Firm* — MH2 Technology Law Group LLP (57) ABSTRACT

A circuit arrangement for an optical monitoring system comprises a driver circuit configured to generate at least one driving signal for driving a light source and a detector terminal for receiving a detector current. The circuit arrangement further comprises a current source configured and arranged to generate at the detector terminal a reduction current. The reduction current has an amplitude which is given by a base value whenever none of the least one driving signal assumes a value suitable for activating the light source and by a sum of the base value and a reduction value otherwise. The circuit arrangement also comprises a pro- (Continued)

cessing unit configured to generate an output signal depending on a combination of the detector current and the reduction current.

21 Claims, 2 Drawing Sheets

(51) Int. Cl.
*A61B 5/00* (2006.01)
*H04B 10/07* (2013.01)

(58) Field of Classification Search
CPC ....... A61B 5/0245; A61B 5/72; A61B 5/7203; H04B 10/07
See application file for complete search history.

(56) References Cited

U.S. PATENT DOCUMENTS

| | | | |
|---|---|---|---|
| 7,148,667 B2 * | 12/2006 | Umemoto | H02M 3/156 323/282 |
| 7,415,256 B2 * | 8/2008 | Nakano | G01N 27/12 455/130 |
| 8,586,912 B1 | 11/2013 | Palmer et al. | |
| 8,587,274 B2 * | 11/2013 | Strydom | H02M 3/158 323/282 |
| 8,766,154 B2 * | 7/2014 | Schweninger | G01S 7/497 250/205 |
| 8,779,858 B2 | 7/2014 | Niederberger et al. | |
| 8,848,202 B2 | 9/2014 | Dyer et al. | |
| 9,018,860 B2 * | 4/2015 | Kado | H02M 3/158 315/307 |
| 9,405,211 B2 * | 8/2016 | Fujita | G03G 15/04054 |
| 2003/0069486 A1 | 4/2003 | Sueppel et al. | |
| 2009/0134860 A1 | 5/2009 | Umemoto et al. | |
| 2011/0062929 A1 | 3/2011 | Strydom et al. | |
| 2012/0188292 A1 | 7/2012 | Inoue et al. | |
| 2013/0094025 A1 | 4/2013 | Nishida et al. | |
| 2013/0181613 A1 | 7/2013 | Schweninger | |
| 2014/0070713 A1 | 3/2014 | Kado | |
| 2015/0015143 A1 * | 1/2015 | Inada | H05B 45/37 315/77 |

FOREIGN PATENT DOCUMENTS

| | | |
|---|---|---|
| CN | 102025277 A | 4/2011 |
| CN | 103154769 A | 6/2013 |
| CN | 103687189 A | 3/2014 |
| CN | 104771140 A | 7/2015 |
| JP | 2014103321 A | 6/2014 |

OTHER PUBLICATIONS

Buttle, Ken et al.: "A Multirate Transceiver IC for Four-Wire Full-Duplex Data Transmission" IEEE Dec. 1991; vol. 26, No. 12; 0018-9200/91/1928-1935.

* cited by examiner

CIRCUIT ARRANGEMENT FOR AN OPTICAL MONITORING SYSTEM AND METHOD FOR OPTICAL MONITORING

BACKGROUND OF THE INVENTION

The present disclosure relates to a circuit arrangement for an optical monitoring system, in particular for an optical monitoring system for monitoring or measuring a biological parameter, and to a method for optical monitoring, in particular for monitoring or measuring a biological parameter.

Photoplethysmography, PPG, may be used for example for monitoring or measuring a biological parameter, for example of a person, such as heart rate, pulse rate variability or oxygen saturation in the blood. PPG signals are for example obtained by injecting a light signal by shining light onto a target region of the person's skin, for example by means of a light emitting diode, LED, and measuring a reflected and/or transmitted signal in close proximity, for example about 2.5 mm using for example green light, of the position of the light signal injection.

PPG techniques may rely on very small physical changes in the thickness and/or volume of blood vessels. Consequently, the obtained PPG signal may have a very high DC or average component but a low AC or fluctuating component. A typical PPG signal obtained for example from light injection at the wrist of a person and corresponding measurement may have a modulation index in the order of a fraction of 1%, for example in the order of 0.05%—0.3%. Therefore, a signal quality of the PPG signal may be of particular importance for monitoring or measuring the biological parameter by means of PPG.

SUMMARY OF THE INVENTION

The present disclosure provides an improved concept for optical monitoring of a biological parameter, in particular by means of PPG, that leads to an improved signal quality, in particular PPG signal quality.

Since the fluctuating component of the PPG signal may be of particular relevance for the monitoring or measurement, low noise and/or high amplification may be required. Such high amplification, however, may bear the risk of running into saturation of the internal signal processing. In addition, ambient light may impair the measurement, for example due to saturation of internal signal processing.

According to the improved concept, signal noise may be reduced and higher signal amplification may be used, resulting in an improved signal quality.

According to the improved concept, a current source, in particular a low current and low noise current source, is connected to the input side of a PPG system. The current source generates a reduction current that reduces a detector current obtained from an optical detector. Therein, the reduction current is modulated according to a driving signal for driving a light source, such that the reduction of the detector current is stronger whenever the light source is activated compared to the opposite case. Consequently, a lower average component of signals is achieved allowing for higher amplification and leading to less noise of the system.

According to the improved concept, a circuit arrangement for an optical monitoring system is provided. The circuit arrangement comprises a driver circuit configured to generate at least one driving signal for driving a light source and a detector terminal for receiving a detector current, in particular from an optical detector. The circuit arrangement further comprises a current source configured and arranged to generate at the detector terminal a reduction current.

The reduction current has an amplitude which is given by a base value whenever none of the least one driving signal assumes a value suitable for activating the light source. On the other hand, the amplitude of the reduction current is given by a sum of the base value and a reduction value otherwise, that is whenever the at least one driving signal, in particular any of the at least one driving signal, assumes a value suitable for activating the light source. The circuit arrangement also comprises a processing unit configured to generate an output signal depending on a combination of the detector current and the reduction current.

In this way, the detector current is effectively reduced by the sum of the base value and the reduction value when the at least one driving signal assumes a value suitable for activating the light source and by the base value otherwise. In particular, reduction by the base value may account for ambient light reaching the optical detector, while reduction by the reduction value may account for additional light, for example excess light, from the light source reaching the optical detector.

This may result in a reduction of an average component of signals, for example the output signal or a signal depending on the detector current and the reduction current. Thus signal quality may be improved due to lower noise and/or higher possible signal amplification.

The optical monitoring system may for example be a photoplethysmography, PPG, system for example for monitoring and/or measuring a biological parameter, for example of a person. In particular, the optical monitoring system may be a heart rate monitoring, HRM, system, for measuring and/or monitoring a heart rate, a pulse or heart rate variability, PRV, system for measuring and/or monitoring a pulse or heart rate variability and/or a pulse oximetry system for measuring and/or monitoring oxygen saturation, SpO2, in the blood.

Above and in the following, "light" refers to electromagnetic radiation in general and to visible light, ultraviolet radiation and/or infrared radiation in particular. In particular, the light source is configured to emit light with at least one specified wavelength spectrum, for example in the visible, ultraviolet and/or infrared spectrum. The specified wavelength spectrum may for example correspond to green light of for example 525 nm, which may result in a particularly good output signal.

Above and in the following, "optical" is related to electromagnetic radiation in general and to visible light, ultraviolet radiation and/or infrared radiation in particular. In particular, the optical monitoring system may operate based on generation, detection and/or processing of such electromagnetic radiation.

According to some implementations of the circuit arrangement, the optical detector is configured to detect electromagnetic radiation, for example visible light, ultraviolet radiation and/or infrared radiation and to generate the detector current based on the detected electromagnetic radiation. In particular, the optical detector may be sensitive to such type of electromagnetic radiation that may be emitted by the light source.

According to some implementations of the circuit arrangement, an output of the current source is connected to the detector terminal for generating the reduction current.

According to some implementations of the circuit arrangement, a current direction, in particular with respect to the detector terminal, of the reduction current is opposed to a current direction, in particular with respect to the detector terminal, of the detector current. That is, the combination of the detector current and the reduction current, which may constitute an input current of the circuit arrangement, has an absolute value that is smaller than an absolute value of the detector current if an absolute value of the reduction current is non-zero.

The at least one driving signal assuming a value suitable for activating the light source means that the least one driving signal assumes value that may cause, in particular causes, the light source to emit light.

According to some implementations of the circuit arrangement, an input current of the circuit arrangement is constituted by the combination of the detector current and the reduction current, in particular by a sum of the detector current and the reduction current.

According to some implementations of the circuit arrangement, the at least one driving signal corresponds to at least one driving current or controls the at least one driving current for driving the light source. In such implementations, the at least one driving signal assumes a value suitable for activating the light source if the driving current is sufficiently high such that the light source may emit light.

According to some implementations of the circuit arrangement, the base value is equal to zero. According to some implementations of the circuit arrangement, the base value is non-zero.

According to some implementations of the circuit arrangement, the reduction value is equal to zero or may be regulated to zero. According to some implementations of the circuit arrangement, the reduction value is non-zero.

According to some implementations of the circuit arrangement, the base value and the reduction value are both positive.

According to some implementations of the circuit arrangement, the light source is not comprised by the circuit arrangement.

According to some implementations of the circuit arrangement, the optical detector is not comprised by the circuit arrangement.

In particular, the circuit arrangement and in particular the driver circuit may be adapted to operate in combination with different types of light sources and/or optical detectors According to some implementations of the circuit arrangement, the optical detector comprises at least one photodetector, for example a photodiode.

According to some implementations of the circuit arrangement, the circuit arrangement comprises the light source and the light source comprises at least one optical emitter configured and arranged to be driven by at least one driving signal.

According to some implementations of the circuit arrangement, the at least one optical emitter comprises at least one LED.

According to some implementations of the circuit arrangement, the at least one optical emitter and/or the at least one LED is configured to emit visible light, for example red visible light, green visible light, blue visible light, yellow visible light or visible light with another color and/or spectrum, and/or infrared radiation.

According to some implementations of the circuit arrangement, the light source may comprise a plurality of optical emitters, for example a plurality of LEDs, wherein different optical emitters of the plurality of optical emitters are configured to emit light of the same or of different spectra.

According to some implementations of the circuit arrangement, each of the optical emitters comprised by the light source is associated to one of the at least one driving signal and is driven by the associated driving signal.

In implementations, wherein the light source comprises a plurality of optical emitters, each of the optical emitters of the plurality of optical emitters may be utilized for different applications of the circuit arrangement and/or to optical monitoring system. An optical emitter, for example an LED, configured to emit green or yellow visible light may for example be utilized to monitor a heart rate for example at a wrist of a person. An optical emitter, for example an LED, configured to emit red visible or infrared light may for example be used for pulse oximetry. Each of the optical emitters may be associated to an individual current reduction setting, in particular an individual reduction value.

According to some implementations of the circuit arrangement, the driver circuit is configured to generate the at least one driving signal as a first and at least a second driving signal. The reduction value is given by a first value, that is a first reduction value, whenever the first signal assumes a value suitable for activating the light source. The reduction value is given by a second value, that is a second reduction value, whenever the second driving signal assumes a value suitable for activating the light source. The first and the second reduction value may be equal to or different from each other.

According to some implementations of the circuit arrangement, a first optical emitter of the light source is driven by the first driving signal and a second optical emitter of the light source is chosen by the second driving signal.

According to some implementations of the circuit arrangement, the circuit arrangement comprises the light source and the light source comprises a first optical emitter configured and arranged to be driven by the first driving signal and a second optical emitter configured and arranged to be driven by the second driving signal.

According to some implementations of the circuit arrangement, the driver circuit is configured to generate the first and the second driving signal such that, at a given time, at most one of the at least one driving signal assumes a value suitable for activating the light source.

According to some implementations of the circuit arrangement, the second reduction value is different from the first reduction value. Consequently, an optimum value for the reduction value may be adjusted for each driving signal and/or optical emitter separately. This may be particularly beneficial for further improvement of signal quality and/or reduction of power consumption.

According to some implementations of the circuit arrangement, the driver circuit is configured to generate the first and the second driving signal such that, at a given time, at most one of the first and the second driving signal assumes a value suitable for activating the light source.

According to some implementations of the circuit arrangement, the circuit arrangement comprises the optical detector.

According to some implementations of the circuit arrangement, the driver circuit comprises at least one driver current source for driving the light source depending on the at least one driving signal.

According to some implementations of the circuit arrangement, wherein the light source comprises a plurality of optical emitters, the driver circuit comprises a plurality of driver current sources, wherein each of the plurality of driver current sources is associated to one of the plurality of optical emitters and vice versa for driving the associated optical emitter.

According to some implementations of the circuit arrangement, the current source is configured and arranged to generate at the detector terminal the reduction current, wherein an amplitude of the reduction current is given by the base value whenever the light source does not emit light and by the sum of the base value and the reduction value whenever the light source, in particular an optical emitter comprised by the light source, does emit light.

In implementations wherein the light source comprises a plurality of optical emitters, the amplitude of the reduction current is given by the base value whenever none of the optical emitters of the plurality of optical emitters does emit light. The amplitude of the reduction current is given by the sum of the base value and the reduction value whenever any of the optical emitters of the plurality of optical images does emit light.

According to some implementations of the circuit arrangement, the processing unit is configured to generate an intermediate signal by amplifying the combination of the detection current and the reduction current, in particular amplifying the input current. The processing unit is configured to determine a first value of the intermediate signal at a first point in time and a second value of the intermediate signal at a second point in time.

Therein, the amplitude of the reduction current is given by the sum of the base value and the reduction value at the first point in time and by the base value at the second point in time. That is, at the first point in time, the at least one driving signal, in particular one of the at least one driving signal, assumes a value suitable for activating the light source and at the second point in time, none of the at least one driving signal assumes a value suitable for activating the light source.

The processing unit is configured to determine a difference between the first and the second value of the intermediate signal and to generate the output signal depending on the determined difference. In this way, the output signal is generated based on a demodulated signal, since otherwise the signal fluctuations due to the pulses driving of the light source may be too high.

In this way, ambient light rejection may be achieved, making the system more independent with respect to environmental variations or fluctuations.

According to some implementations of the circuit arrangement, the circuit arrangement, for example the processing unit, further comprises an amplifier circuit configured and arranged to generate the intermediate signal by amplifying the combination of the detection current and the reduction current, for example the input current. The processing unit is configured to generate the output signal based on the intermediate signal.

According to some implementations of the circuit arrangement, the amplifier circuit comprises a transimpedance amplifier, TIA, with a first input connected to the detector terminal for receiving the combination of the detection current and the reduction current, for example input current.

According to some implementations of circuit arrangement, the TIA comprises an output connected to the processing unit for supplying the intermediate signal.

According to some implementations of the circuit arrangement, the TIA comprises a second input connected to a reference terminal.

According to some implementations of the circuit arrangement, the processing unit is configured to determine a level of signal quality based on the output signal and/or on the intermediate signal and to adapt the reduction value and/or the at least one driving signal, in particular an amplitude, for example a maximum amplitude, of the at least one driving signal, depending on the level of signal quality.

In such implementations, in particular the reduction value and/or the driving current may be reduced if the level of signal quality is more than sufficiently high for a given application. In this way, a power consumption of the circuit arrangement may be reduced.

According to some implementations of the circuit arrangement, the processing unit is configured to adapt the reduction value by decreasing an absolute value of the reduction value if the level of signal quality lies above a predefined first quality threshold value.

According to some implementations of the circuit arrangement, the processing unit is configured to reduce a driving current associated to the at least one driving signal if the level of signal quality lies above a predefined second quality threshold value. The second quality threshold value may be equal to or different from the first quality threshold value.

According to some implementations of the circuit arrangement, the level of signal quality is given by a signal-to-noise ratio of the intermediate signal and/or the output signal and/or a signal depending on the output signal.

According to some implementations of the circuit arrangement, the circuit arrangement, for example the processing unit, is configured to generate a motion compensated signal based on the output signal by accounting for effects on the detector current and/or the output signal caused by a motion of the person and/or the circuit arrangement.

According to some implementations of the circuit arrangement, the level of signal quality is given by a signal amplitude of the motion compensated signal and/or by a signal-to-noise ratio of the motion compensated signal.

According to some implementations of the circuit arrangement, the level of signal quality is given by a signal quality indicator, SQI, derived from the output signal.

According to some implementations of the circuit arrangement, the level of signal quality and/or the SQI is derived from the output signal. The level of signal quality and/or the SQI may for example be derived from a heart signal, a frequency variation, a heart frequency variation, an amplitude variation, a heart amplitude variation and/or another quantity and/or signal derived from the output signal.

According to some implementations of the circuit arrangement, the circuit arrangement, for example the processing unit, further comprises a control unit configured and arranged to determine, at a time when the amplitude of the reduction current is given by the sum of the base value and the reduction value, whether a value of a signal depending on the input current lies within a predefined first range.

According to some implementations of the circuit arrangement, the control unit is configured and arranged to determine, at a time when the light source does emit light, whether the value of the signal depending on the input current lies within the predefined first range.

According to some implementations of the circuit arrangement, the control unit is configured and arranged to determine, at a time when the amplitude of the reduction current is given by the base value, whether the value of the signal depending on the input current lies within a predefined second range.

According to some implementations of the circuit arrangement, the control unit is configured and arranged to determine, at a time when the light source does not emit light, whether the value of the signal depending on the input current lies within the predefined second range.

According to some implementations of the circuit arrangement, the signal depending on the input current is the intermediate signal.

According to some implementations of the circuit arrangement, the control unit is configured to adapt the reduction value if it is determined that the value of the signal depending on the input current does not lie within the first range.

In such implementations, the reduction value may be dynamically adapted to environmental conditions. For example the reduction value may be reduced when signal quality of the output signal is reduced due to a too little or a too large amount of light reaching the optical detector. In turn, signal quality may be further improved in such implementations.

According to some implementations of the circuit arrangement, the control unit is configured to increase the absolute value of the reduction value if the value of the signal depending on the input current lies above the first range and/or to decrease the absolute value of the reduction value if the value of the signal depending on the input current lies below the first range or vice versa.

According to some implementations of the circuit arrangement, the control unit is configured to adapt the base value if it is determined that the value of the signal depending on the input current does not lie within the second range.

In such implementations, the base value may be dynamically adapted to environmental conditions, in particular to changing ambient light conditions. For example the base value may be reduced the when ambient light becomes less and/or increased when the ambient light becomes more. In turn, signal quality may be further improved in such implementations.

According to some implementations of the circuit arrangement, the control unit is configured to increase the absolute value of the base value if the value of the signal depending on the input current lies above the second range and/or to decrease the absolute value of the base value if the value of the signal depending on the input current lies below the second range or vice versa.

According to some implementations of the circuit arrangement, the control unit is configured to adapt an amplification factor of the amplifier circuit if it is determined that the value of the signal depending on the input current does not lie within the first range and/or does not lie within the second range.

In such implementations, the base value may be dynamically adapted to environmental conditions, for example to changing ambient light conditions. For example, since the effective reduction of the detector current by the base value reduces an influence of ambient light, the amplification factor may be increased. This may result in a reduced signal-to-noise ratio and increased fluctuating component for example of the intermediate and/or the output signal and consequently in a further improved signal quality.

According to some implementations of the circuit arrangement, the control unit is configured to increase the amplification factor if the value of the signal depending on the input current lies below the first range and/or to decrease the amplification factor if the value of the signal depending on the input current lies above the first range or vice versa.

According to some implementations of the circuit arrangement, the control unit is configured to increase the amplification factor if the value of the signal depending on the input current lies below the second range and/or to decrease the amplification factor if the value of the signal depending on the input current lies above the second range or vice versa.

According to some implementations of the circuit arrangement, the control unit is configured to adapt at least one driving signal, in particular a maximum amplitude of the at least one driving signal, if the value of the signal depending on the input current does not lie within the first range and/or does not lie within the second range.

In such implementations, the at least one driving signal and/or driving current may be dynamically adapted, for example when signal quality of the output signal is reduced due to a too little or a too large amount of light reaching the optical detector and/or when the ambient light conditions change. In turn, signal quality may be further improved in such implementations.

According to some implementations of the circuit arrangement, the control unit is configured to increase a driving current for the light source if the value of the signal depending on the input current lies below the first and/or the second range and to decrease the driving current for the light source if the value of signal depending on the input current lies above the first and/or the second range or vice versa.

According to some implementations of the circuit arrangement, the combination of the detector current and the reduction current, for example the input current, is a sum of the detector current and the reduction current. An absolute value of the sum is smaller than an absolute value of the detector current.

According to some implementations of the circuit arrangement, the output signal is a PPG signal or a signal suitable for generating a PPG signal.

According to the improved concept, also a method for optical monitoring is provided. The method comprises generating at least one driving signal, for example at least one driving current, for driving a light source, receiving a detector current from an optical detector and generating a reduction current. An amplitude of the reduction current is given by a base value whenever none of the at least one driving signal assumes a value suitable for activating the light source. The amplitude of the reduction current is given by a sum of the base value otherwise, that is whenever the at least one driving signal, in particular any of the at least one driving signal, assumes a value suitable for activating the light source. The method further comprises generating an output signal depending on a combination of the detector current and the reduction current, for example depending on an input current depending on a combination of detector current and the reduction current.

The optical monitoring may comprise heart rate monitoring, HRM, pulse or heart rate variability, PRV, monitoring, and/or pulse oximetry.

According to some implementations of the method, the method further comprises illuminating a target region of an object by means of light emitted by the light source and detecting a fraction of the light being reflected and/or transmitted by the target region and/or a region of the object being adjacent to the target region. The method comprises generating the detector current based on the detected fraction of the light.

According to some implementations of the method, the reduction current is generated with the amplitude of the reduction current being given by the base value whenever the light source does not emit light and by the sum of the base value and the reduction value whenever the light source, in particular an optical emitter comprised by the light source, does emit light.

Further implementations of the method are readily derived from the various implementations and embodiments of the circuit arrangement and vice versa.

BRIEF DESCRIPTION OF THE DRAWINGS

In the following, the invention is explained in detail with the aid of exemplary implementations by reference to the drawings. Components that are functionally identical or have an identical effect may be denoted by identical references.

Identical components and/or components with identical effects may be described only with respect to the figure where they occur first and their description is not necessarily repeated in subsequent figures.

In the drawings.

DETAILED DESCRIPTION

Figure 1:
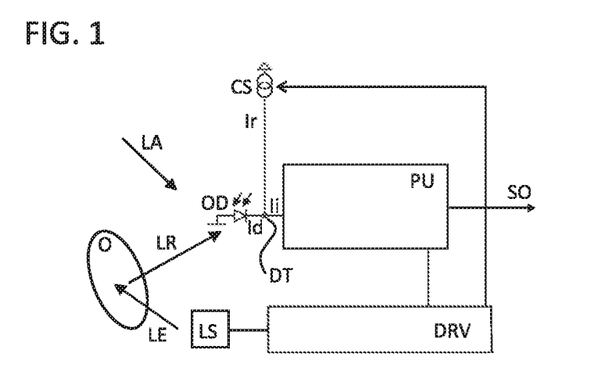
FIG. 1 shows an exemplary implementation of a circuit arrangement according to the improved concept.

FIG. 1 shows an exemplary implementation of a circuit arrangement according to the improved concept. The circuit arrangement comprises a driver circuit DRV, a processing unit PU connected to the driver circuit DRV and to a detector terminal DT, and a current source CS connected to the detector terminal DT. Furthermore, an optical detector OD connected to the detector terminal DT as well as a light source LS connected to the driver circuit DRV are shown. The optical detector OD and the light source LS may be comprised by the circuit arrangement. In alternative implementations the optical detector OD and/or the light source LS are not comprised by circuit arrangement.

Moreover, an object O, which is not comprised by the circuit arrangement, as well as an emitted light signal LE, a response light signal LR and an ambient light signal LA are shown. The object O may for example be a body part or a part of a body part of a person or animal. The object O may for example be a wrist of a person. For operation, the circuit arrangement and/or the light source LS and the optical detector OD may for example be arranged in close proximity or in contact to the object O.

The driver circuit DRV may for example generate a driving signal or a plurality of driving signals for driving the light source LS. The driving signal or the plurality of driving signals may for example correspond to a driving current or a plurality of driving currents, respectively, for the light source LS. Based on the driving signal, the light source LS may generate the emitted light signal LE which may illuminate a target region of the object O. In particular, the driving signal may be a pulsed signal that may for example change back and forth between an off-level and an on-level, in this way generating the emitted light signal LE in a pulsed manner. In particular when the driving signal assumes the on-level, the light source LS may be activated, that is may emit light. When the driving signal assumes the off-level, for example is equal to zero, the light source LS may not be activated, that is may not emit light.

In this way, the emitted light signal LE features on-phases when the driving signal assumes the on-level and the light source LS emits light and off-phases when the driving signal assumes the off-level and the light source LS does not emit light.

A pulse frequency of the driving signal may for example lie between several Hz and several kHz, for example between 20 Hz and 1 kHz. In some implementations, the pulse frequency may be adjustable. Consequently, a switching frequency of the light source LS, in particular frequency of switching between the off-phase and the on-phase, may be given by or approximately given by the pulse frequency of the driving signal.

A pulse frequency of the driving signal may for example lie between several Hz and several kHz, for example between 20 Hz and 1 kHz. In some implementations, the pulse frequency may be adjustable. Consequently, a switching frequency of the light source LS, in particular frequency of switching between the off-phase and the on-phase, may be given by or approximately given by the pulse frequency of the driving signal.

The light signal may hit the target region of the object O and may be reflected and/or transmitted, in particular partially reflected and/or transmitted, by the object O, for example by the target region and/or a region adjacent to the target region resulting in a response light signal LR. The response light signal LR may for example be detected by the optical detector OD.

Furthermore, the optical detector OD may also detect an ambient light signal LA. The ambient light signal LA may for example originate from ambient light that may or may not be present in an environment of the circuit arrangement and/or the object O.

The optical detector OD may for example be implemented as a photodetector, for example a photodiode. In particular, the optical detector OD may be implemented as a photodetector sensitive to light being emitted by the light source, in particular sensitive to the emitted light signal LE.

Based on the detected response light signal LR and/or the detected ambient light signal LA, the optical detector OD may generate a detector current Id at the detector terminal DT. The current source CS may generate a reduction current Ir at the detector terminal DT, wherein an amplitude of the reduction current Ir depends on the driving signal and/or on the emitted light signal LE. Depending on the optical detector OD, the amplitude of the reduction current Ir may for example lie in the order of tens or hundreds of nA, for example in the order of 50 nA or 100 nA.

In particular, during periods when the light source LS emits light, the amplitude of the reduction current Ir is different than during periods when the light source LS does not emit light. That is, amplitude of the reduction current Ir may be modulated according to the driving signal, in particular synchronously with the driving signal switching between the on-level and the off-level. In other words, the reduction current Ir may be modulated according to and/or synchronous to the switching of the light source LS.

In particular, the amplitude of the reduction current Ir is different during off-phases of the emitted light signal LE than during on-phases of the emitted light signal LE. That is, the amplitude of the reduction current Ir is different during periods when the driving signal assumes the on-level than during periods when the driving signal assumes the off-level. In particular, an absolute value of the reduction current Ir may be smaller during the off-phases of the emitted light signal LE, that is when the driving signal assumes the off-level, than during the on-phases of the emitted light signal LE, that is when driving signal assumes the on-level.

At the detector terminal DT, the detector current Id and the reduction current Ir are combined resulting in an input current Ii being supplied to the processing unit PU. The processing unit PU then generates an output signal SO based on the input current Ii. The output signal SO is for example a photoplethysmogram, PPG, signal or a signal suitable for generating a PPG signal.

The current source CS may for example be implemented as a programmable current source and may for example be controlled by the processing unit PU and/or the driver circuit DRV to generate the reduction current Id as described above. The driver circuit DRV may in particular control a timing of the current source CS. That is, the control driver circuit DRV may control the current source CS to generate the reduction current Ir having an amplitude given by a base value whenever the driving signal assumes the off-level, that is during off-phases of the emitted light signal LE. Furthermore, the driver circuit DRV may control the current source CS to generate the reduction current Ir having an amplitude given by a sum of the base value and a reduction value whenever the driving signal assumes the on-level, that is during on-phases of the emitted light signal LE. An absolute value of the reduction current Ir may for example always be smaller than an absolute value of the detector current Id.

Alternatively or in addition, the current source LS may comprise a first and a second current source CS1, CS2 (not shown in FIG. 1, see FIGS. 2 and 3), wherein the first current source CS1 is configured to generate a current having an amplitude given by the sum of the base value and the reduction value and the second current source CS2 is configured to generate a current having an amplitude given by the base value. In such implementations, the processing unit PU and/or the driver circuit DRV may be configured to control the current source CS such that it generates the reduction current Id by means of the first current source CS1 during the on-phases of the emitted light signal LE and by means of the second current source CS2 during the off-phases of the emitted light signal LE.

The current direction of the reduction current Ir is such that the reduction current Ir is effectively subtracting from the detector current Id detector terminal DT. That is, the current direction of the reduction current Ir is such that an absolute value of the input current Ii is always equal to or smaller than an absolute value of the detector current Id. In particular, with ∥ denoting the absolute value, the following relations hold: |Ii|=|Id|−|Ir| and |Ir|<|Id|.

The reduction of the detector current Id by the reduction current Ir may be less during the off-phases than during the on-phases of the emitted light signal LE. This is for example due to the fact that the response light signal LR and consequently the detector current Id may be significantly larger during the on-phases than during the off-phases, since during the on-phases more light reaches the optical detector OD. The reduction of the detector current Id by the reduction current Ir may also be zero during the off-phases of the emitted light signal LE.

The output signal SO may then be used to determine, measure and/or monitor a biological parameter of the person or animal, such as heart rate, pulse rate variability and/or oxygen saturation, SpO2. In case of monitoring or measuring SpO2, a value corresponding to the reduction value and/or the reduction current Ir may have to be added mathematically to the output signal SO or to a signal depending on the output signal, since SpO2 measurements may rely on the average as well as on the fluctuating signal components.

Figure 2:
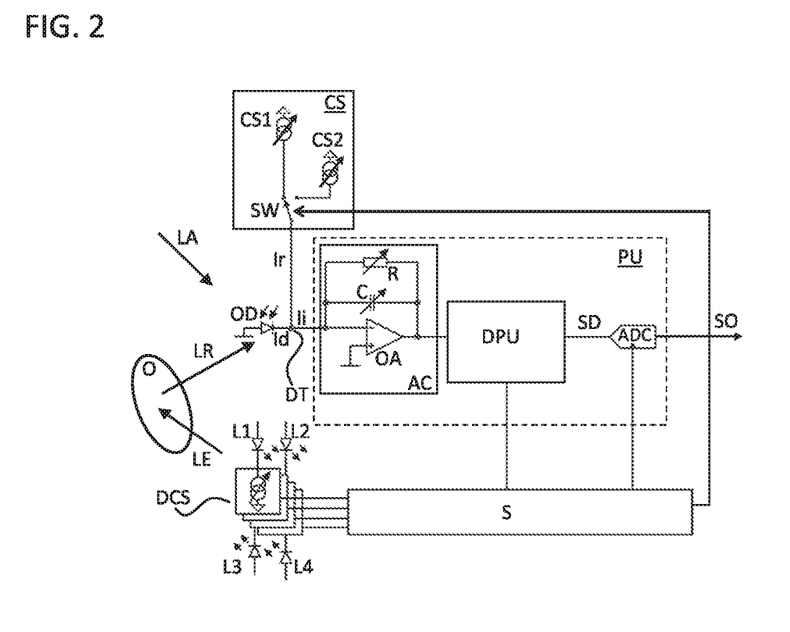
FIG. 2 shows a further exemplary implementation of a circuit arrangement according to the improved concept.

FIG. 2 shows a further exemplary implementation of a circuit arrangement according to the improved concept. The implementation of FIG. 2 is based on the implementation of FIG. 1.

The processing unit PU comprises an amplifier circuit AC with an input side connected to the detector terminal DT, and a demodulation and signal processing unit DPU connected to an output side of the amplifier circuit AC. The processing unit PU also comprises an analog-to-digital converter ADC connected through the stimulation and signal processing unit DPU.

The amplifier circuit AC is for example implemented and connected as a transimpedance amplifier, TIA, and comprises an operational amplifier OA with a first input, for example an inverting input, connected to the detector terminal DT and with a second input, for example a non-inverting input, connected to a reference terminal. The amplifier circuit AC comprises a capacitor C, for example a tunable capacitor, connected between the first input of the operational amplifier OA and an output of the operational amplifier OA. The amplifier circuit AC further comprises a resistor R, for example a tunable resistor, connected between the first input and the output of the operational amplifier OA. In alternative implementations of the circuit arrangement, the amplifier circuit AC comprises only one of the resistor R and the capacitor C. By tuning a resistance of the resistor R and/or a capacitance of the capacitor C, an amplification factor of the amplifier circuit AC may be tuned.

The current source CS may be optimized with respect to noise. In particular a corresponding signal-to-noise ratio of the circuit arrangement may be significantly smaller than a modulation index of the PPG signal, for example smaller by a factor 2 or 5 than a modulation index in the order of 0.05%—0.3%.

In the example of FIG. 2, the driver circuit DRV comprises a sequencer S and four driver current sources FCS. For the sake of clarity, only one of the driver current sources FCS is shown. The light source LS comprises a first, a second, a third and a fourth optical emitter L1, L2, L3, L4. The optical emitters L1, L2, L3, L4 are for example implemented as LEDs. Each of the optical emitters L1, L2, L3, L4 is connected to an associated one of the driver current sources FCS. In particular, the first optical emitter L1 is connected to a first driver current source, the second optical emitter L2 is connected to a second driver current source, the third optical emitter L3 is connected to a third driver current source and the fourth optical emitter L4 is connected to a fourth driver current source.

The sequencer S is connected to each of the driver current sources FCS. The sequencer S is also connected to the demodulation and signal processing unit DPU and to the analog-to-digital converter ADC.

The example of FIG. 2, the current source CS comprises a first current source CS1, a second current source CS2 and a switch SW. The first current source CS1 may be configured to generate a current with an amplitude given by the sum of the base value and the reduction value and the second current source CS2 is configured to generate a current with an amplitude given by the base value. The switch SW may for example be controlled by the sequencer S to connect the detector terminal DT to the first current source CS1 during on-phases of the emitted light signal LE and to the second current source CS2 during off-phases of the emitted light signal LE. The first and/or the second current source may be tunable or programmable for adjusting the base and/or the reduction value.

In alternative implementations, the current source CS may be implemented as a programmable current source as described with respect to FIG. 1.

The sequencer S may control the first driver current source such that it generates a first driving signal, in particular a first driving current, for driving the first optical emitter L1. Analogously, the sequencer S may control the second, third and fourth driver current sources such that they generate a second, a third and a fourth driving signal or driving current for driving the second, the third and fourth optical emitter L2, L3, L4, respectively.

In particular the sequencer S may control the driver current sources FCS such that only one of the optical emitters L 1, L2, L3, L4 may emit light at a given time. Consequently, the operation of the circuit arrangement shown in FIG. 2 is analog to the operation of the circuit arrangement shown in FIG. 1 as explained above. In particular, on-phases of the emitted light signal LE correspond to periods when any of the driving signals assumes a respective on-level suitable for activating the associated optical emitter. Analogously, off-phases of the emitted light signal LE correspond to periods when none of the driving signals assumes a respective on-level, that is when each of the driving signal assumes a respective off-level not suitable for activating the associated optical emitter.

The sequencer S may control the current source CS such that it generates the reduction current Ir having an amplitude given by the sum of the base value and the reduction value whenever any of the driving signals assumes a respective on-level and by the base value otherwise.

The optical emitters L1, L2, L3, L4 may be configured to emit different types of radiation, in particular different colors of light. For example at least one of the optical emitters L1, L2, L3, L4 may be configured to emit green light, at least one of the optical emitters L1, L2, L3, L4 may be configured to emit red light and at least one of the optical emitters L1, L2, L3, L4 may be configured to emit infrared radiation.

In this way, different optical emitters L1, L2, L3, L4 may be used for different applications of the circuit arrangement and to monitoring system, respectively. For example, an optical emitter configured to emit green light may be used for monitoring a heart rate, while an optical emitter configured to emit red light or infrared radiation, may be used for monitoring an oxygen saturation in the blood.

In some implementations, the reduction value may be different, depending on which of the driving signal assumes the respective on-level. That is, in case the first optical emitter L1 emits light, the reduction value may be given by a first reduction value, in case the second optical emitter emits light, the reduction value may be given by a second reduction value and so forth. The first, the second, the third and the fourth reduction value may be equal to or different or partially different from each other.

The amplifier circuit AC amplifies the input current Ii, in this way generating an intermediate signal being supplied to the demodulation and signal processing unit DPU. The demodulation and signal processing unit DPU may generate a demodulated signal SD based on the intermediate signal. To this end, the demodulation and signal processing unit may for example subtract a value of the intermediate signal during an on-phase of the emitted light signal LE and a value of the intermediate signal during an off-phase of the emitted light signal LE from each other. A corresponding timing or clock of the demodulation and signal processing unit DPU may be controlled or provided by the sequencer S.

Furthermore, the demodulation and signal processing unit DPU may comprise one or more filters for generating the demodulated signal SD by filtering the intermediate signal or a signal depending on the intermediate signal.

The demodulated signal is supplied to the analog-to-digital converter ADC. The analog-to-digital converter ADC converts for example the analog the modulated signal SD into the digital output signal SO. A corresponding timing or clock of the analog-to-digital converter ADC of the may be controlled or provided by the sequencer S.

Figure 3:
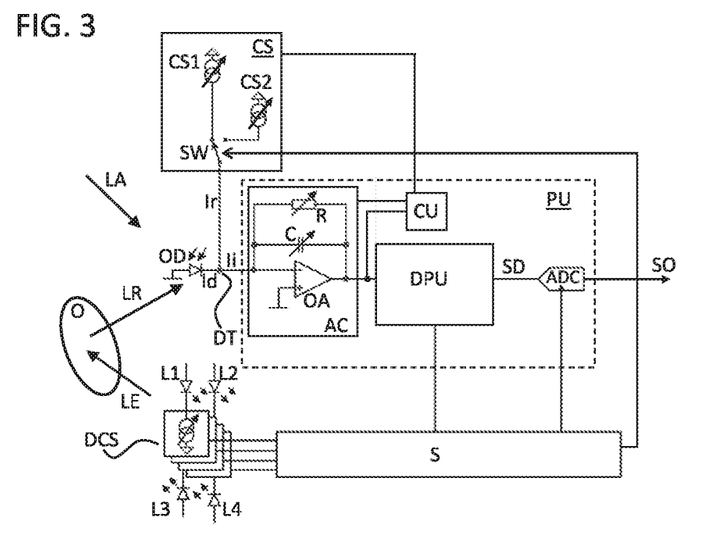
FIG. 3 shows a further exemplary implementation of a circuit arrangement according to the improved concept.

FIG. 3 shows a further exemplary implementation of a circuit arrangement according to the improved concept. The implementation of FIG. 3 is based on the implementation of FIG. 2.

In the implementation of FIG. 3, the processing unit PU further comprises a control unit CU connected between the amplifier circuit AC and the demodulation and signal processing unit DPU for receiving the intermediate signal.

The control unit CU may determine during an on-phase whether the intermediate signal lies within a predefined first range and/or during an off-phase whether the intermediate signal lies within a predefined second range.

The control unit CU may be connected to the amplifier circuit AC and may be configured to tune the amplification factor of the amplifier circuit AC, for example by tuning the capacitance of the capacitor C and/or the resistance of the resistor R, depending on the intermediate signal. If the intermediate signal lies outside the first range during an on-phase and/or outside the second range during an off-phase, the control unit CU may adjust the amplification factor of the amplifier circuit AC accordingly to drive the intermediate signal back into the first and/or the second range.

Alternatively or in addition, the control unit CU may be connected to the current source CS and may be configured to adapt the base value and/or the reduction value. In particular, if the intermediate signal lies outside the first range during an on-phase, the control unit CU may adapt the reduction value and/or the LED current accordingly to drive the intermediate signal back into the first range. This may for example be particularly advantageous in case only a little amount of light is reaching the optical detector OD, for example for very dark skin tone of the person, due to limited coupling efficiency of light into the object O and/or due to limited efficiency of the light source LS.

If the intermediate signal lies outside the second range during an off-phase, the control unit may adapt the base value accordingly to drive the intermediate signal back into the second range. This may for example be particularly advantageous for compensating a changing ambient light condition.

Alternatively or in addition, the control unit may be connected to the driver current sources DCS. This connection is not shown in FIG. 3 the sake of clarity. If the intermediate signal lies outside the first range during an on-phase and/or outside the second range during an off-phase, the control unit CU may adjust the driving signals or driving currents accordingly to drive the intermediate signal back into the first and/or the second range.

Figure 4:
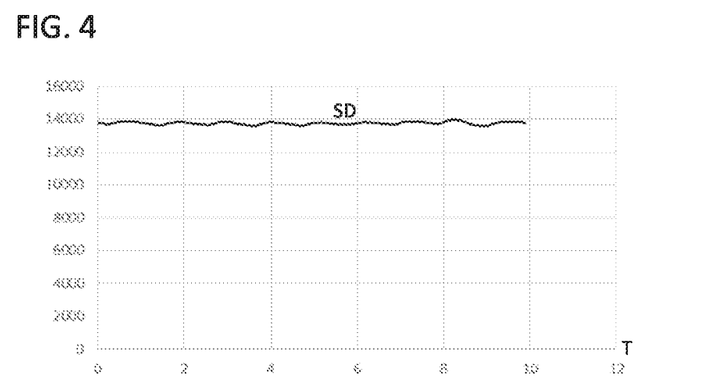
FIG. 4 shows a demodulated signal occurring in a circuit arrangement for an optical monitoring system.

FIG. 4 shows a demodulated signal SD occurring in a circuit arrangement for an optical monitoring system, in particular in a conventional circuit arrangement for an optical monitoring system. The demodulated signal SD shown in FIG. 4 may be understood as demodulated signal SD as occurring in an implementation of one of FIGS. 2 and 3, wherein the current source CS is not present or the reduction current Ir is zero, respectively.

On the horizontal axis, time T is shown in arbitrary units and on the vertical axis the demodulated signal SD is shown in arbitrary units. It can be seen that the fluctuating component of the demodulated signal SD is very small compared to the average component of the demodulated signal SD.

Figure 5:
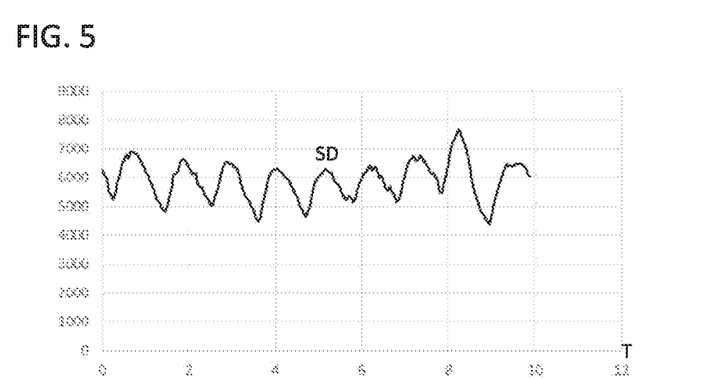
FIG. 5 shows a demodulated signal occurring in a circuit arrangement according to the improved concept.

FIG. 5 shows a demodulated signal occurring in a circuit arrangement according to the improved concept, for example in the circuit arrangement as described with respect to one of FIGS. 2 and 3.

On the horizontal axis, time T is shown in the same arbitrary units as in FIG. 4 and on the vertical axis the demodulated signal SD is shown in the same arbitrary units as an FIG. 4. It can be seen that the average component of the demodulated signal SD is significantly decreased with respect to the example shown in FIG. 4. This is due to the reduction of the detector current Id by the reduction current Ir as described with respect to FIGS. 1 to 3. Consequently, the amplification factor of the amplifier arrangement AC could be increased without the risk of saturation. Therefore, the fluctuating component of the demodulated signal SD is significantly increased with respect to the example shown in FIG. 4.

The curves of the demodulated signal SD shown in FIGS. 4 and 5 are based on actually measured signals.

By means of a circuit arrangement according to the improved concept, an average component of the input current Ii, the output signal SO, the intermediate signal and/or the demodulated signal SD may be reduced due to the reduction of the detector current Id by the reduction current Ir. In particular, the average component may be reduced more during the on-phases than during the off-phases of the emitted light signal LE.

In implementations wherein the base value is non-zero, the average component is reduced during the off-phases of the emitted light signal LE. However, the reduction is less than during the on-phases, that is when any of the at least one driving signal assumes a value suitable for activating the light source. In this way, also impairing influence of ambient light may be reduced.

Furthermore, due to the reduction of the input current Ii, for example during the off-phases, the amplification factor of the amplifier circuit AC may be increased without the risk of saturation. The current consumption and/or the size of the amplifier circuit AC may for example be reduced while obtaining similar or better signal-to-noise ratio.

Also a driving current of the light source LS may be reduced by means of the improved concept since the signal-to-noise ratio, in particular of the whole optical chain of the monitoring system, is improved. This may lead to reduction of power consumption.

Moreover, compared to the average component of the demodulated signal SD, the fluctuating component of the demodulated signal SD is increased in this way, which may relax requirements on the accuracy of the analog-to-digital converter ADC and/or noise requirements for the amplifier circuit AC, in particular the TIA.

Consequently, an improved signal quality, in particular an improved PPG signal quality, may be achieved according to the improved concept.

The invention claimed is:

1. Circuit arrangement for an optical monitoring system, the circuit arrangement comprising
    a driver circuit configured to generate at least one driving signal for driving a light source;
    a detector terminal for receiving a detector current, in particular from an optical detector;
    a current source configured and arranged to generate at the detector terminal a reduction current, wherein an amplitude of the reduction current;
        is given by a base value whenever none of the at least one driving signal assumes a value suitable for activating the light source; and
        is given by a sum of the base value and a reduction value otherwise;
    a processing unit configured to generate an output signal depending on a combination of the detector current and the reduction current; and
    a control unit) configured and arranged to
        determine whether a value of a signal depending on the combination of the detector current and the reduction current lies within a predefined first range at a time when the amplitude of the reduction current is given by the sum of the base value and the reduction value and/or lies within a predefined second range at a time when the amplitude of the reduction current is given by the base value; and
        adapt the at least one driving signal if the value of the signal depending on the combination of the detector current and the reduction current does not lie within the first range and/or does not lie within the second range.

2. Circuit arrangement according to claim 1, wherein the processing unit is configured to generate an intermediate signal by amplifying the combination of the detector current and the reduction current.

3. Circuit arrangement according to claim 2, wherein the processing unit is configured to
    determine a first value of the intermediate signal at a first point in time and a second value of the intermediate signal at a second point in time, wherein amplitude of the reduction current is given by the sum of the base value and the reduction value at the first point in time and by the base value at the second point in time;
    determine a difference between the first and the second value of the intermediate signal; and
    generate the output signal depending on the determined difference.

4. Circuit arrangement according to claim 2, further comprising an amplifier circuit configured and arranged to generate the intermediate signal by amplifying the combination of the detection current and the reduction current, wherein the processing unit is configured to generate the output signal based on the intermediate signal.

5. Circuit arrangement according to claim 4, wherein the amplifier circuit comprises a transimpedance amplifier, TIA, with a first input connected to the detector terminal for receiving the combination of the detection current and the reduction current.

6. Circuit arrangement according to claim 5, wherein the TIA comprises an output connected to the processing unit for supplying the intermediate signal.

7. Circuit arrangement according to claim 4, wherein the control unit is configured to adapt an amplification factor of the amplifier circuit if it is determined that the value of the signal depending on the input current does not lie within the first range and/or does not lie within the second range.

8. Circuit arrangement according to claim 1, wherein the processing unit is configured to determine a level of signal quality based on the output signal and to adapt the reduction value and/or the at least one driving signal depending on the level of signal quality.

9. Circuit arrangement according to claim 8, wherein the level of signal quality is given by
   a signal-to-noise ratio of the intermediate signal and/or the output signal and/or a signal depending on the output signal; or is given by
   a signal quality indicator derived from the output signal.

10. Circuit arrangement according to claim 9, wherein the level of signal quality and/or the signal quality indicator is derived from a heart signal, a heart frequency variation and/or a heart amplitude variation.

11. Circuit arrangement according to claim 1, wherein the control unit is configured to
   adapt the reduction value if the value of the signal depending on the combination of the detector current and the reduction current does not lie within the first range; and/or
   adapt the base value if the value of the signal depending on the combination of the detector current and the reduction current does not lie within the second range.

12. Circuit arrangement according to claim 1, wherein the control unit is configured to adapt a maximum amplitude of the at least one driving signal if the value of the signal depending on the combination of the detector current and the reduction current does not lie within the first range and/or does not lie within the second range.

13. Circuit arrangement according to claim 1, wherein
   the combination of the detector current and the reduction current is a sum of the detector current and the reduction current; and
   an absolute value of the sum is smaller than an absolute value of the detector current.

14. Circuit arrangement according to claim 1, wherein
   the driver circuit is configured to generate the at least one driving signal as a first and at least a second driving signal;
   the reduction value is given by a first reduction value whenever the first driving signal assumes a value suitable for activating the light source; and
   the reduction value is given by a second reduction value whenever the second driving signal assumes a value suitable for activating the light source.

15. Circuit arrangement according to claim 14, wherein the second reduction value is different from the first reduction value.

16. Circuit arrangement according to one of claim 14, further comprising the light source, wherein the light source comprises a first optical emitter configured and arranged to be driven by the first driving signal and a second optical emitter configured and arranged to be driven by the second driving signal.

17. Circuit arrangement according to claim 1, further comprising the light source, wherein the light source comprises at least one optical emitter configured and arranged to be driven by the at least one driving signal.

18. Circuit arrangement according to claim 1, further comprising the optical detector.

19. Circuit arrangement according to claim 1, wherein the output signal is a photoplethysmogram, PPG, signal or a signal suitable for generating a PPG signal.

20. Method for optical monitoring, the method comprising
   generating at least one driving signal for driving a light source;
   receiving a detector current from an optical detector;
   generating a reduction current, wherein an amplitude of the reduction current
      is given by a base value whenever none of the at least one driving signal assumes a value suitable for activating the light source; and
      is given by a sum of the base value and a reduction value otherwise;
   generating an output signal depending on a combination of the detector current and the reduction current;
   determining whether a value of a signal depending on the combination of the detector current and the reduction current lies within a predefined first range at a time when the amplitude of the reduction current is given by the sum of the base value and the reduction value and/or lies within a predefined second range at a time when the amplitude of the reduction current is given by the base value; and
   adapting the at least one driving signal if the value of the signal depending on the combination of the detector current and the reduction current does not lie within the first range and/or does not lie within the second range.

21. Method according to claim 20, further comprising
   illuminating a target region of an object with light emitted by the light source;
   detecting a fraction of the light being reflected from and/or transmitted by the target region and/or a region of the object being adjacent to the target region; and
   generating the detector current based on the detected fraction of the light.

\* \* \* \* \*